US012605522B2

(12) United States Patent
Hattori et al.

(10) Patent No.: US 12,605,522 B2
(45) Date of Patent: Apr. 21, 2026

(54) CPAP APPARATUS

(71) Applicant: Murata Manufacturing Co., Ltd.,
Kyoto (JP)

(72) Inventors: Atsushi Hattori, Kyoto (JP); Hsing Kenghua, Kyoto (JP)

(73) Assignee: Murata Manufacturing Co., Ltd.,
Kyoto (JP)

( * ) Notice: Subject to any disclaimer, the term of this patent is extended or adjusted under 35 U.S.C. 154(b) by 574 days.

(21) Appl. No.: 18/302,850

(22) Filed: Apr. 19, 2023

(65) Prior Publication Data

US 2023/0338679 A1    Oct. 26, 2023

(30) Foreign Application Priority Data

Apr. 20, 2022    (JP) ................................. 2022-069454

(51) Int. Cl.
*A61M 16/16*       (2006.01)
*A61M 16/00*       (2006.01)
*A61M 16/08*       (2006.01)

(52) U.S. Cl.
CPC ........ *A61M 16/16* (2013.01); *A61M 16/0066* (2013.01); *A61M 16/0816* (2013.01)

(58) Field of Classification Search
CPC .. A61M 16/00; A61M 16/0057; A61M 16/10; A61M 16/1045; A61M 16/1075; A61M 16/108; A61M 16/1085; A61M 16/14; A61M 16/16; A61M 16/0816; A61M 16/0066; A61M 2205/123
See application file for complete search history.

(56) References Cited

U.S. PATENT DOCUMENTS

| | | | | | |
|---|---|---|---|---|---|
| 3,804,280 | A | * | 4/1974 | van Amerongen | ...... B65D 1/06 128/200.11 |
| 4,152,379 | A | * | 5/1979 | Suhr | ..................... A61M 16/16 261/DIG. 65 |
| 5,564,415 | A | * | 10/1996 | Dobson | ............... A61M 16/109 220/795 |
| 6,398,197 | B1 | * | 6/2002 | Dickinson | ............. A61M 16/16 261/DIG. 65 |
| 9,155,858 | B2 | * | 10/2015 | Chen | ................... A61M 16/109 |
| 9,737,680 | B2 | * | 8/2017 | Hsiao | .................. A61M 16/109 |
| 11,738,166 | B2 | * | 8/2023 | Smith | .................. A61M 16/16 128/200.24 |

(Continued)

FOREIGN PATENT DOCUMENTS

| | | |
|---|---|---|
| JP | 2005-188780 A | 7/2005 |
| JP | 2016-512706 A | 5/2016 |

(Continued)

*Primary Examiner* — Colin W Stuart
(74) *Attorney, Agent, or Firm* — McDonald Hopkins LLC

(57)        ABSTRACT

A humidifying tank of a CPAP apparatus includes a first passage, a second passage, a flow-dividing section, and a shielding section. An inlet is defined as an opening of the first passage on an inner space side, an outlet is defined as an opening of the second passage on the inner space side, and a vertical axis is defined as a specific axis that intersects a bottom wall. As seen in a direction along the vertical axis, an opening center of the outlet is located so as to be displaced relative to an imaginary axis that passes through an opening center of the inlet and that is parallel to a direction in which the inlet faces.

8 Claims, 3 Drawing Sheets

(56)        References Cited

U.S. PATENT DOCUMENTS

| | | | |
|---|---|---|---|
| 2007/0230927 A1* | 10/2007 | Kramer | A61M 16/16 |
| | | | 392/403 |
| 2009/0194106 A1* | 8/2009 | Smith | A61M 16/0616 |
| | | | 128/203.16 |
| 2010/0154796 A1* | 6/2010 | Smith | A61M 16/0066 |
| | | | 239/311 |
| 2011/0155132 A1 | 6/2011 | Virr et al. | |
| 2012/0266880 A1* | 10/2012 | Young | A61M 16/1075 |
| | | | 128/203.26 |
| 2015/0202402 A1* | 7/2015 | Kat | A61M 16/0066 |
| | | | 128/203.27 |
| 2016/0022954 A1 | 1/2016 | Bath et al. | |
| 2017/0361053 A1 | 12/2017 | Dimatteo et al. | |
| 2021/0093825 A1* | 4/2021 | Lin | A61M 16/1095 |
| 2021/0283361 A1* | 9/2021 | Zhuang | A61M 16/00 |
| 2022/0265954 A1* | 8/2022 | Tyke | A61M 16/109 |
| 2023/0030885 A1 | 2/2023 | Hattori et al. | |

FOREIGN PATENT DOCUMENTS

| | | | |
|---|---|---|---|
| JP | 2017-121502 A | 7/2017 |
| JP | 2017-537708 A | 12/2017 |
| WO | 2021/205913 A1 | 10/2021 |

* cited by examiner

CPAP APPARATUS

CROSS REFERENCE TO RELATED APPLICATION

This application claims priority from Japanese Patent Application No. 2022-069454 filed on Apr. 20, 2022. The content of this application is incorporated herein by reference in its entirety.

BACKGROUND OF THE DISCLOSURE

1. Field of the Disclosure

The present disclosure relates to a continuous positive airway pressure (CPAP) apparatus.

2. Description of the Related Art

A CPAP apparatus described in Japanese Unexamined Patent Application Publication No. 2017-537708 includes a blower and a humidifying tank. The blower pressurizes and feeds air to an inner space of the humidifying tank. The humidifying tank can store water in the inner space. The humidifying tank has a first passage and a second passage. The first passage is a passage for guiding air, pressurized and fed by the blower, to the inner space. The second passage is a passage for guiding air in the inner space to the outside of the humidifying tank.

In a CPAP apparatus configured as described in Japanese Unexamined Patent Application Publication No. 2017-537708, a flow-dividing section may be provided in the humidifying tank. The flow-dividing section faces an opening of the first passage on the inner space side. In this case, the air that has flowed into the inner space from the opening of the first passage on the inner space side collides with the flow-dividing section. The air collided with the section is divided into flows in a plurality of directions, and flows to an opening of the second passage on the inner space side.

Here, the air, whose flow has been divided, is humidified with the water stored in the inner space of the humidifying tank. Accordingly, in order to appropriately humidify the air to be guided out of the second passage, it is necessary to ensure a sufficiently long time for the air to flow from the first passage to the second passage. However, depending the route of the air, whose flow has been divided, the air might not be sufficiently humidified.

BRIEF SUMMARY OF THE DISCLOSURE

In order to solve the above problem, a CPAP apparatus according to the present disclosure includes: a blower that pressurizes and feeds air; and a humidifying tank that allows air, pressurized and fed by the blower, to flow thereinto and has an inner space that is capable of storing water. The humidifying tank includes: a top wall, a side wall, and a bottom wall that define the inner space; a first passage through which the blower communicates with the inner space; a second passage through which the inner space communicates with a portion that is outside of the humidifying tank and that is different from the blower; a flow-dividing section that faces an inlet when the inlet is defined as an opening of the first passage on the inner space side; and a shielding section that extends toward the flow-dividing section from an end surface of the first passage on a side in which the inlet is open. When an outlet is defined as an opening of the second passage on the inner space side and a vertical axis is defined as a specific axis that intersects the bottom wall, as seen in a direction along the vertical axis, an opening center of the outlet is located so as to be displaced relative to an imaginary axis that passes through an opening center of the inlet and that is parallel to a direction in which the inlet faces. When a specific end is defined as an end that is one of two ends of the inlet in a direction along an orthogonal axis orthogonal to the vertical axis and that is near the opening center of the outlet when the inlet is seen in a direction along the imaginary axis, the shielding section extends to the flow-dividing section from a portion that is included in the end surface and that is further toward an opposite side from the opening center of the inlet than the specific end.

With the configuration described above, the air that has flowed into the inner space from the inlet collides with the flow-dividing section. When the flow of the air that has collided with the flow-dividing section is diverted, the shielding section blocks a flow of the air toward the outlet. Therefore, the air, whose flow has been divided, is restrained from passing along the shortest route toward the outlet. Thus, it is possible to provide a sufficient length to a route along which the air, whose flow has been divided, flows. As the route of the air can have a sufficient length in this way, the air flows in the humidifying tank for a long time, and thus it become easy for the air guided to the outside of the humidifying tank to be humidified.

It becomes easy for the air guided to the outside of the humidifying tank to be humidified.

DETAILED DESCRIPTION OF THE DISCLOSURE

Embodiment

Figure 1:
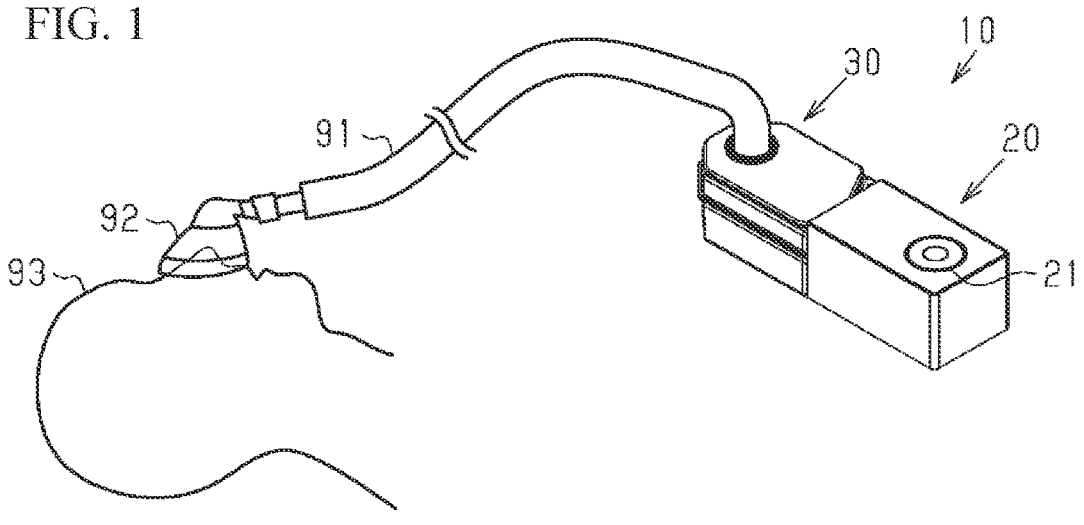
FIG. 1 illustrates a state in which a CPAP apparatus is being used.

Hereafter, a CPAP apparatus according to an embodiment will be described. In the drawings, some elements may be enlarged for ease of understanding. The dimensional ratios of elements may differ from actual ones or from those in other figures.

Overall Configuration

Referring to FIG. 1, the overall configuration of a continuous positive airway pressure apparatus (hereafter, referred to as a CPAP apparatus) will be described.

As illustrated in FIG. 1, a CPAP apparatus 10 includes a blower 20, a humidifying tank 30, a hose 91, and a mask 92.

The blower 20 is substantially shaped like a box. The blower 20 includes a blower fan for pressurizing and feeding air. The blower 20 has an air passage through which air flows between the inside and outside of the box. Illustration of the air passage is omitted in FIG. 1. The blower 20 has a switch 21. The switch 21 is located on an upper surface of the blower 20. The switch 21 is operated to control ON/OFF of the blower fan of the blower 20 and the like.

The humidifying tank 30 is connected to the blower 20. To be specific, the humidifying tank 30 is connected to the air passage of the blower 20. The humidifying tank 30 can store water in the inside thereof. The air that has been pressurized and fed from the blower fan of the blower 20 can flow to the inside of the humidifying tank 30.

The hose 91 is connected to the humidifying tank 30 at a position different from a position where the blower 20 is connected to the humidifying tank 30. The air that has passed through the inside of the humidifying tank 30 and has been humidified flows through the inside of the hose 91.

The mask 92 is connected to an end of the hose 91 opposite to an end on the humidifying tank 30 side. The mask 92 is worn by a user 93 so as to cover the nose or the mouth of the user 93. That is, the user 93 inhales the humidified air via the hose 91 and the mask 92.

Humidifying Tank

Figure 2:
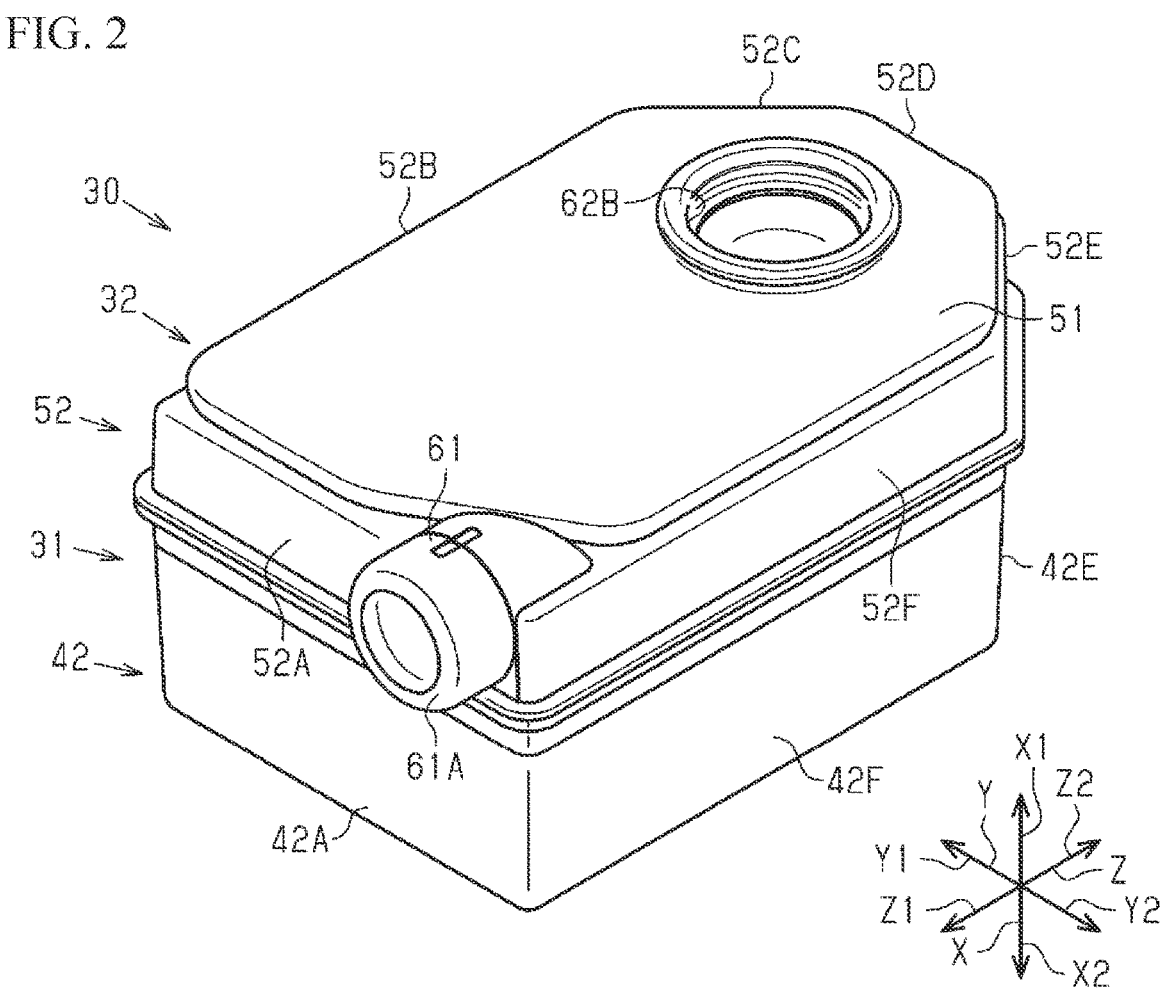
FIG. 2 is a perspective view of a humidifying tank.
Figures 4, 5:
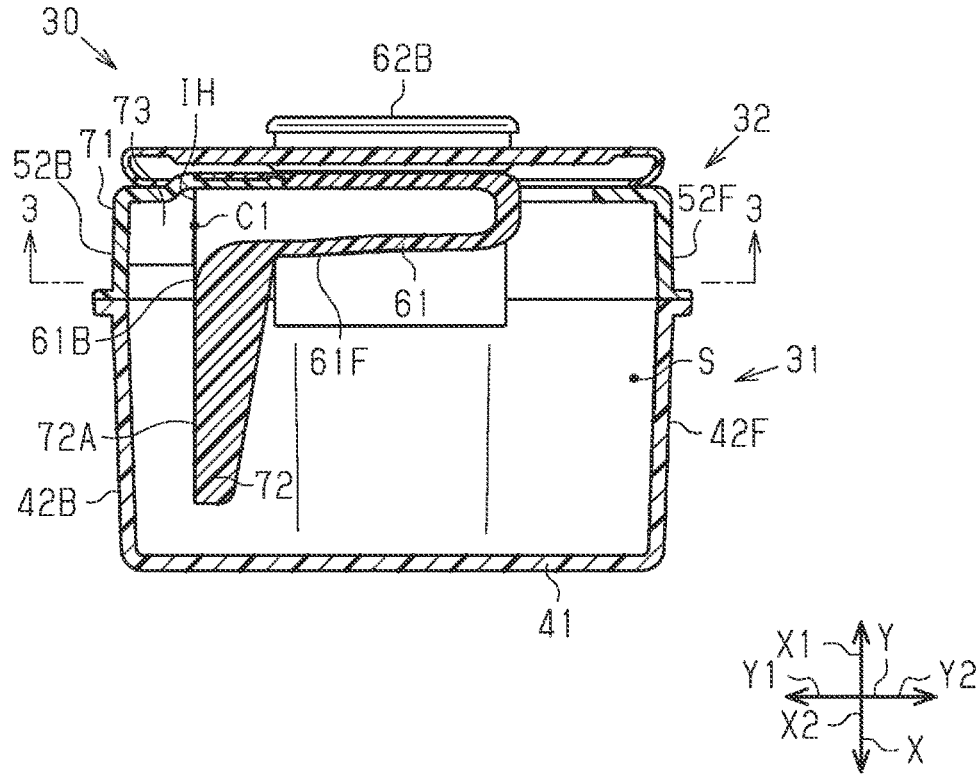
FIG. 4 is a sectional view of the humidifying tank taken along line IV-IV in FIG. 3.
FIG. 5 is a sectional view of the humidifying tank taken along line V-V in FIG. 4.

As illustrated in FIG. 2, the humidifying tank 30 has a tank portion 31 and a cover portion 32. As illustrated in FIG. 5, the tank portion 31 and the cover portion 32 define an inner space S of the humidifying tank 30.

As illustrated in FIG. 2, the tank portion 31 is shaped like a box that has a bottom and one side of which is open. That is, the tank portion 31 has a bottom wall 41 and a lower side wall 42 standing on the bottom wall 41.

The bottom wall 41 is shaped like a flat plate. When seen in a direction orthogonal to the bottom wall 41, the bottom wall 41 has a shape that is elongated in one direction. To be specific, when seen in the direction orthogonal to the bottom wall 41, the bottom wall 41 has a shape such that two of the four corners of a rectangle are chamfered. Accordingly, when seen in the direction orthogonal to the bottom wall 41, the bottom wall 41 has a hexagonal shape having six sides.

Here, a first axis X is defined as an axis orthogonal to the bottom wall 41. A second axis Y is defined as an axis orthogonal to the first axis X. In the present embodiment, the second axis Y is an axis extending in the transversal direction of the bottom wall 41. A third axis Z is defined as an axis orthogonal to the first axis X and the second axis Y. In the present embodiment, the third axis Z is an axis extending in the longitudinal direction of the bottom wall 41. A first positive direction X1 is defined as one of the two directions along the first axis X, and a first negative direction X2 is defined as the other direction opposite to the first positive direction X1. A second positive direction Y1 is defined as one of the two directions along the second axis Y, and a second negative direction Y2 is defined as the other direction opposite to the second positive direction Y1. A third positive direction Z1 is defined as one of the two directions along the third axis Z, and a third negative direction Z2 is defined as the other direction opposite to the third positive direction Z1. The humidifying tank 30 is used in a position such that the first positive direction X1 is the upward direction and the first negative direction X2 in the downward direction.

The lower side wall 42 stands in the first positive direction X1 on the edge of the bottom wall 41. The lower side wall 42 extends along the entire edge of the bottom wall 41. To be specific, the lower side wall 42 has a first lower side wall 42A, a second lower side wall 42B, a third lower side wall 42C, a fourth lower side wall (not shown), a fifth lower side wall 42E, and a sixth lower side wall 42F.

The first lower side wall 42A stands in the first positive direction X1 on an edge of the bottom wall 41 on the third positive direction Z1 side. The first lower side wall 42A is a wall orthogonal to the third axis Z.

The second lower side wall 42B stands in the first positive direction X1 on an edge of the bottom wall 41 on the second positive direction Y1 side. The second lower side wall 42B is a wall orthogonal to the second axis Y.

The third lower side wall 42C stands in the first positive direction X1 on an edge of the bottom wall 41 between the edge on the second positive direction Y1 side and an edge on the third negative direction Z2 side. That is, the third lower side wall 42C stands on an edge of a chamfered portion of the bottom wall 41. The third lower side wall 42C is a wall parallel to the first axis X. The third lower side wall 42C is inclined relative to both of the second axis Y and the third axis Z.

The fourth lower side wall (not shown) stands in the first positive direction X1 on the edge of the bottom wall 41 on the third negative direction Z2 side. The fourth lower side wall (not shown) is a wall orthogonal to the third axis Z. That is, the fourth lower side wall (not shown) is parallel to the first lower side wall 42A.

The fifth lower side wall 42E stands in the first positive direction X1 on an edge of the bottom wall 41 between the edge on the third negative direction Z2 side and an edge on the second negative direction Y2 side. That is, the fifth lower side wall 42E stands on an edge of a chamfered portion of the bottom wall 41. The fifth lower side wall 42E is a wall parallel to the first axis X. The fifth lower side wall 42E is inclined relative to both of the second axis Y and the third axis Z.

The sixth lower side wall 42F stands in the first positive direction X1 on the edge of the bottom wall 41 on the second negative direction Y2 side. The sixth lower side wall 42F is a wall orthogonal to the second axis Y. That is, the sixth lower side wall 42F is parallel to the second lower side wall 42B.

The cover portion 32 has an upper cover 51 and an upper side wall 52. The cover portion 32 covers the opening of the tank portion 31 on the first positive direction X1 side.

When seen in a direction along the first axis X, the outer shape of the upper cover 51 is the same as that of the bottom wall 41. That is, the bottom wall 41 has a shape such that two corners of a rectangle are chamfered. The upper cover 51 and the bottom wall 41 face each other in the direction along the first axis X. In the present embodiment, the first axis X, which is orthogonal to the bottom wall 41 and the upper cover 51, is the vertical axis. A direction from the upper cover 51 toward the bottom wall 41 is the downward direction. A direction from the bottom wall 41 toward the upper cover 51 is the upward direction.

The upper side wall 52 stands in the first negative direction X2 on the edge of the upper cover 51. The upper side wall 52 extends along the entire edge of the upper cover 51. To be specific, the upper side wall 52 has a first upper side wall 52A, a second upper side wall 52B, a third upper side wall 52C, a fourth upper side wall 52D, a fifth upper side wall 52E, and a sixth upper side wall 52F.

The first upper side wall 52A stands in the first negative direction X2 on an edge of the upper cover 51 on the third positive direction Z1 side. The first upper side wall 52A is a wall orthogonal to the third axis Z.

The second upper side wall 52B stands in the first negative direction X2 on an edge of the upper cover 51 on the second positive direction Y1 side. The second upper side wall 52B is a wall orthogonal to the second axis Y.

The third upper side wall 52C stands in the first negative direction X2 on an edge of the upper cover 51 between the edge on the second positive direction Y1 side and an edge on the third negative direction Z2 side. That is, the third upper side wall 52C stands on an edge of a chamfered portion of the upper cover 51. The third upper side wall 52C is a wall parallel to the first axis X. The third upper side wall 52C is inclined relative to both of the second axis Y and the third axis Z.

The fourth upper side wall 52D stands in the first negative direction X2 on the edge of the upper cover 51 on the third negative direction Z2 side. The fourth upper side wall 52D is a wall orthogonal to the third axis Z. That is, the fourth upper side wall 52D is parallel to the first upper side wall 52A.

The fifth upper side wall 52E stands in the first negative direction X2 on an edge of the upper cover 51 between the edge on the third negative direction Z2 side and an edge on the second negative direction Y2 side. That is, the fifth upper side wall 52E stands on an edge of a chamfered portion of the upper cover 51.

The sixth upper side wall 52F stands in the first negative direction X2 on the edge of the upper cover 51 on the second negative direction Y2 side. The sixth upper side wall 52F is a wall orthogonal to the second axis Y. That is, the sixth upper side wall 52F is parallel to the second upper side wall 52B.

An end of the upper side wall 52 on the first negative direction X2 side is connected with an end of the lower side wall 42 on the first positive direction X1 side. To be specific, the first upper side wall 52A is connected with the first lower side wall 42A. The second upper side wall 52B is connected with the second lower side wall 42B. The third upper side wall 52C is connected with the third lower side wall 42C. The fourth upper side wall 52D is connected with the fourth lower side wall (not shown). The fifth upper side wall 52E is connected with the fifth lower side wall 42E. The sixth upper side wall 52F is connected with the sixth lower side wall 42F. The upper side wall 52 and the lower side wall 42 constitute the side wall of the humidifying tank 30.

Passages

Figure 3:
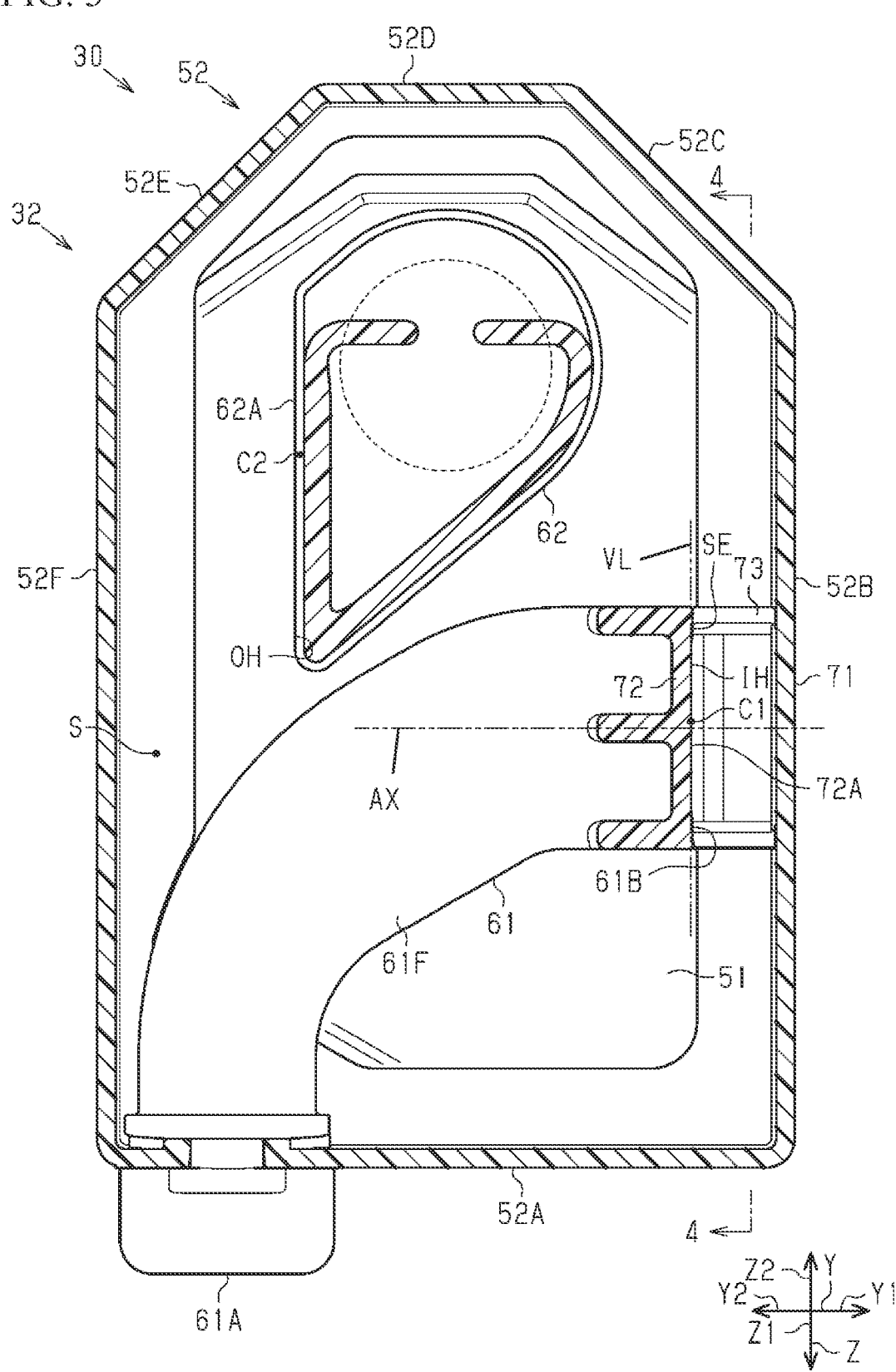
FIG. 3 is a sectional view of the humidifying tank taken along line III-III in FIG. 5.

As illustrated in FIG. 3, the cover portion 32 has a first passage 61 and a second passage 62.

The first passage 61 has a tubular shape. The first passage 61 extends through the first upper side wall 52A. Through the first passage 61, the blower 20 communicates with the inner space S. That is, the first passage 61 is a path for guiding air, pressurized and fed by the blower 20, to the inner space S of the humidifying tank 30. The first passage 61 is made of a material different from that of the cover portion 32.

The outer surface of the first passage 61 has an outer peripheral surface 61F, a first end surface 61A, and a second end surface 61B. The first end surface 61A is an end surface on the blower 20 side in the direction in which the first passage 61 extends. The second end surface 61B is an end surface on the inner space S side in the direction in which the first passage 61 extends. The outer peripheral surface 61F is a part of the outer surface excluding the first end surface 61A and the second end surface 61B. The outer peripheral surface 61F is located in the inner space S, and faces in the first negative direction X2. The outer peripheral surface 61F connects the first end surface 61A and the second end surface 61B. The first passage 61 is open in the first end surface 61A and in the second end surface 61B.

As illustrated in FIG. 3, a part of the first passage 61 including the first end surface 61A is located outside of a space defined by the first to sixth upper side walls 52A to 52F. The shape of an opening in the first end surface 61A of the first passage 61 is substantially circular. The opening in the first end surface 61A of the first passage 61 faces in the third positive direction Z1. The first end surface 61A of the first passage 61 is connected to the blower 20.

The direction in which an opening faces is determined as follows. First, a viewpoint from which the apparent opening area of the opening is the maximum as seen from the outside is determined. Then, the direction in which the opening faces is defined as a direction toward the viewpoint from the geometric center of the opening as seen from the viewpoint. The opening center of the opening is defined as the geometric center.

As illustrated in FIG. 4, the second end surface 61B of the first passage 61 is located in the inner space S of the humidifying tank 30. In particular, an end of the opening in the second end surface 61B of the first passage 61 on the first negative direction X2 side is located further toward the upper cover 51 side than the center of the inner space S. The shape of the opening in the second end surface 61B of the first passage 61 is substantially quadrangular.

The opening in the second end surface 61B of the first passage 61 faces in the second positive direction Y1. That is, as illustrated in FIG. 3, when the cover portion 32 is seen in the first positive direction X1, the first passage 61 is curved by 90 degrees from the first end surface 61A toward the second end surface 61B. The opening in the second end surface 61B of the first passage 61 faces the second upper side wall 52B. The opening in the second end surface 61B of the first passage 61, that is, the opening on the inner space S side is an inlet IH of air.

As illustrated in FIGS. 2 and 3, the second passage 62 has a tubular shape. The second passage 62 extends through the upper cover 51. Through the second passage 62, the inner space S communicates with a portion that is outside of the humidifying tank 30 and that is different from the blower 20. That is, the second passage 62 is a path for guiding air in the inner space S of the humidifying tank 30 to the outside of the humidifying tank 30.

The second passage 62 is integrally formed with the upper cover 51. A part of the outer surface of the second passage 62 faces the bottom wall 41 in a direction along the second axis Y. That is, the second passage 62 and the upper cover 51 constitute a top wall of the humidifying tank 30. The top wall, the aforementioned side wall, and the bottom wall 41 define the inner space S.

A first end 62A of the second passage 62 is located in the inner space S of the humidifying tank 30. The shape of an opening at the first end 62A of the second passage 62 is substantially quadrangular. The opening at the first end 62A of the second passage 62 faces in the second negative direction Y2. The opening at the first end 62A of the second passage 62, that is, the opening of the second passage 62 on the humidifying tank 30 side is an outlet OH of air.

As illustrated in FIG. 2, a second end 62B of the second passage 62 is located outside of the humidifying tank 30. The shape of an opening at the second end 62B of the second passage 62 is substantially circular. The opening at the second end 62B of the second passage 62 faces in the first positive direction X1. That is, the second passage 62 is curved by 90 degrees from the first end 62A toward the second end 62B. Accordingly, the second passage 62 extends so as to be located gradually in the first positive direction X1 with increasing distance from the first end 62A toward the second end 62B. The second end 62B of the second passage 62 is connected to the hose 91.

Flow-Dividing Section

As illustrated in FIG. 3, the humidifying tank 30 has a flow-dividing section 71. The flow-dividing section 71 faces the opening in the second end surface 61B of the first passage 61, that is, the inlet IH. In the present embodiment, the flow-dividing section 71 is a part of the side wall. To be specific, among the side walls, the second upper side wall 52B is the flow-dividing section 71.

Facing Section

As illustrated in FIG. 5, the humidifying tank 30 has a facing section 72. The facing section 72 extends toward the bottom wall 41 from the outer peripheral surface 61F of the first passage 61. In particular, the facing section 72 extends toward the bottom wall 41 from a portion that is included in the outer peripheral surface 61F of the first passage 61 and that overlaps the opening in the second end surface 61B of the first passage 61 when seen along the first axis X.

As illustrated in FIG. 4, the dimension of the facing section 72 in the direction along the third axis Z is slightly larger than the dimension of the inlet IH in the direction along the third axis Z. The facing section 72 is present over the entire area of the inlet IH in the direction along the third axis Z.

As illustrated in FIG. 5, the facing section 72 extends to a position further toward the bottom wall 41 side than the center of the inner space S in the direction along the first axis X. The facing section 72 has a facing surface 72A. The facing surface 72A is a surface facing in a direction that is the same as the direction in which the inlet IH faces. The facing surface 72A is a portion that overlaps the opening in the second end surface 61B when seen along the first axis X. The facing section 72 is connected to an outer surface of the first passage 61 on the first negative direction X2 side via a plurality of ribs.

Positional Relationship Between Inlet and Outlet

As illustrated in FIG. 3, an imaginary axis AX is defined as an axis that passes through the opening center C1 of the inlet IH and that is parallel to the second axis Y when the humidifying tank 30 is seen in the first positive direction X1. The opening center C2 of the outlet OH is located so as to be displaced relative to the imaginary axis AX when the humidifying tank 30 is seen in the first positive direction X1. In other words, the opening center C2 of the outlet OH is not present on the imaginary axis AX. The opening center C2 of the outlet OH is located on the third negative direction Z2 side relative to the imaginary axis AX.

As illustrated in FIG. 4, a specific end SE is defined as an end that is one of the two ends of the inlet IH in the direction along the third axis Z and that is near the opening center C2 of the outlet OH when the humidifying tank 30 is seen in the second negative direction Y2. At this time, the specific end SE is located on the outer side of the curve of the first passage 61, that is, on the third negative direction Z2 side. In the present embodiment, the third axis Z is an orthogonal axis orthogonal to the first axis X, which is the vertical axis, as seen in the direction along the second axis Y.

Here, an imaginary straight line VL is defined as an imaginary straight line that extends on the facing surface 72A. When the humidifying tank 30 is seen in the first negative direction X2, the outlet OH is located on the opposite side from the direction in which the inlet IH faces, that is, on the second negative direction Y2 side with respect to the imaginary straight line VL.

Shielding Section

As illustrated in FIG. 5, the humidifying tank 30 has a shielding section 73. The shielding section 73 extends toward the flow-dividing section 71 from the second end surface 61B of the first passage 61. The specific end SE is located further toward the third negative direction Z2 side than the opening center C1 of the inlet IH in the direction along the third axis Z. At this time, the shielding section 73 extends to the flow-dividing section 71 from a portion that is included in the second end surface 61B of the first passage 61 and that is further toward the opposite side from the opening center C1 of the inlet IH than the specific end SE.

As illustrated in FIG. 4, the dimension of the shielding section 73 in the direction along the first axis X is ½ or more of the dimension of the inlet IH in the direction along the first axis X. An end of the shielding section 73 on the first positive direction X1 side is connected to an inner surface of the upper cover 51. An end of the shielding section 73 on the first negative direction X2 side is located on the first negative direction X2 side as seen from the opening center C1 of the inlet IH. That is, the shielding section 73 is present from an end of the inlet IH on the first positive direction X1 side in a region that is a half or more of the inlet IH in the direction along the first axis X. The end of the shielding section 73 on the first negative direction X2 side does not reach the center of the inner space S in the direction along the first axis X.

On the other hand, when the humidifying tank 30 is seen in the first negative direction X2, the shielding section 73 is not provided on a portion that is further toward the opposite side from the opening center C1 of the inlet IH than an end that is one of the two ends of the inlet IH and that is not the specific end SE. That is, when the humidifying tank 30 is seen in the first negative direction X2, the shielding section 73 is located only on a portion that is included in the second end surface 61B of the first passage 61 and that is further toward the opposite side from the opening center C1 of the inlet IH than the specific end SE. Therefore, when the humidifying tank 30 is seen in the first negative direction X2, among portions that are outside of both ends of the inlet IH, the distance between the bottom wall 41 and one of the portions that is far from the opening center C2 of the outlet OH is longer than the distance between the bottom wall 41 and the other portion that is near the opening center C2.

Operations of Present Embodiment

When using the CPAP apparatus 10, the CPAP apparatus 10 is placed on a desk or the like so that the first positive direction X1 of the CPAP apparatus 10 coincides with the upward direction and the first negative direction X2 of the CPAP apparatus 10 coincides with the downward direction. When using the CPAP apparatus 10, water is stored in the inner space S of the humidifying tank 30. At this time, water is supplied in an amount with which the inner space S is filled up to approximately the center of the inner space S in the direction along the first axis X. In this case, an end of the facing section 72 on the first negative direction X2 side is immersed in water.

When the switch 21 is pressed, the blower 20 is driven, and the compressed air is fed from the blower fan. The air passes through the first passage 61 of the humidifying tank 30, and flows into the humidifying tank 30.

The air that has flowed into the humidifying tank 30 flows in a space that is included in the inner space S of the humidifying tank 30 and that is on the first positive direction X1 side as seen from the water surface. At this time, as illustrated in FIG. 3, the flow of the air that has entered from the inlet IH of the second end surface 61B of the first passage 61 is divided by colliding with the flow-dividing section 71.

Effects of Present Embodiment (1) With the embodiment described above, when the flow of the air that has collided with the flow-dividing section 71 is divided, the shielding section 73 blocks the flow of the air toward the outlet OH. Therefore, the air, whose flow has been divided, is restrained from passing along the shortest route toward the outlet OH. Thus, it is possible to provide a sufficient length to a route through which the air, whose flow has been divided, flows. As the route of the air can have a sufficient length in this way, the air flows in the humidifying tank 30 for a long time, and thus it becomes easy for the air guided to the outside of the humidifying tank 30 to be humidified.

(2) In the embodiment described above, by flowing in the first passage 61, the flow of the air that enters from the inlet IH is directed toward the outer side of the curve of the first passage 61 due to the centrifugal force. Therefore, if the shielding section 73 were not provided, the air that has flowed out from the second end 62B of the second passage 62 would tend to flow in the third negative direction Z2 when the humidifying tank 30 is seen in the first negative direction X2. That is, the air that has flowed out from the second end 62B of the second passage 62 would tend to flow toward the outlet OH along the shortest distance. With the embodiment described above, the shielding section 73 is located on the outer side of the curve of the first passage 61. Thus, it is possible to obtain a significant effect of the shielding section 73 in blocking the flow of the air along the shortest distance.

(3) In the embodiment described above, the flow-dividing section 71 is a part of the side wall. That is, by using a part of the side wall as the flow-dividing section 71, it is not necessary to additionally provide the flow-dividing section 71. As a result, it is possible to prevent the reduction in the amount of water that can be stored in the inner space S.

(4) With the embodiment described above, the dimension of the shielding section 73 in the direction along the first axis X is ½ or more of the dimension of the inlet IH in the direction along the first axis X. Therefore, the shielding section 73 extends in the direction along the first axis X with a sufficient length, and thus it is possible to more reliably block the flow of the air along the shortest distance.

(5) With the embodiment described above, the facing surface 72A of the facing section 72 faces the flow-dividing section 71. Therefore, the air that has entered from the inlet IH collides with the flow-dividing section 71, and then the air generates a tumble flow, having a rotation axis parallel to the third axis Z, between the flow-dividing section 71 and the facing surface 72A. Due to the tumble flow, the air repeatedly flows multiple times near the water surface of the inner space S. Thus, it becomes easier for the air to be humidified from the water surface in the inner space S.

(6) If a large number of tumble flows were generated in the entirety of the inner space S, the water surface of water stored in the inner space S would rise and fall, and water would easily flow into the second passage 62. In this regard, with the embodiment described above, the facing section 72 extends to a position further toward the bottom wall 41 side than the center of the inner space S in the direction along the first axis X. Therefore, a portion where such a tumble flow may be generated is limited to a portion between the flow-dividing section 71 and the facing surface 72A. That is, it is possible to prevent excessive rising and falling of the water surface of water due to the generation of a large number of tumble flows.

(7) Moreover, with the embodiment described above, the facing section 72 extends toward the bottom wall 41 from a portion that is included in the outer peripheral surface 61F of the first passage 61 and that overlaps the inlet IH when seen in the first negative direction X2. Therefore, the distance between the facing surface 72A and the flow-dividing section 71 is comparatively short, and thus it is possible to further limit the portion where a tumble flow may be generated.

(8) With the embodiment described above, when the humidifying tank 30 is seen in the first negative direction X2, the outlet OH is located on the opposite side from the direction in which the inlet IH faces with respect to the imaginary straight line VL. Thus, the air that has flowed from the inlet IH in the second positive direction Y1 does not collide with the flow-dividing section 71, and the probability that the air straightly reaches the outlet OH is low. In this way, by causing the air to collide with the flow-dividing section 71 without fail, it is possible to reduce the flow speed of the air and to increase the distance to the outlet OH. As a result, it becomes easier for the air to be humidified.

Other Embodiments

The embodiment described above and modifications described below can be used in combination as long as technological contradiction does not occur.

In the embodiment described above, the CPAP apparatus 10 may have any configuration provided that the CPAP apparatus has the blower 20 and the humidifying tank 30. The shape of the entirety of the CPAP apparatus 10 is not limited.

In the embodiment described above, the configuration of the humidifying tank 30 is not limited. For example, the tank portion 31 and the cover portion 32 may be integrally formed, and a part of the side wall of the tank portion 31 may be open. The upper cover 51 included in the top wall may be curved, and each wall included in the side wall may be curved.

In the embodiment described above, the humidifying tank 30 may be quadrangular or may be circular when seen in the direction along the first axis X.

In the embodiment described above, the first passage 61 may be integrally formed with the cover portion 32. It is sufficient that the first passage 61 has a tubular shape and has the second end surface 61B.

In the embodiment described above, the shape of the first passage 61 is not limited, as long as air can flow through the inside thereof. For example, the cross section of the first passage 61 may be uniform from the first end surface 61A to the second end surface 61B. A part of the path of the first passage 61 may be formed by the upper cover 51. The first passage 61 may extend linearly.

The curving angle of the first passage 61 is not limited to 90 degrees. The first passage 61 need not be curved. For example, the first passage 61 may be linear when the humidifying tank 30 is seen in the first negative direction X2.

The orientation in which the first passage 61 is curved is not limited to the example in the embodiment described above. The specific end SE may be located on the inner side of the first passage 61 when the humidifying tank 30 is seen in the first negative direction X2.

In the embodiment described above, the shape of the second passage 62 is not limited, as long as air can flow through the inside thereof. For example, the path cross section of the second passage 62 may be uniform from the first end 62A to the second end 62B. The second passage 62 may extend linearly and parallel to the upper cover 51. That is, the second end 62B of the second passage 62 may protrude from the side wall of the tank portion 31. The second passage 62 may be curved toward the first negative direction X2 from the first end 62A of the second passage 62 toward the downstream side.

When the humidifying tank 30 is seen in the first negative direction X2, the outlet OH may be located on the same side as the direction in which the inlet IH faces with respect to the imaginary straight line VL. When the humidifying tank 30 is seen in the first negative direction X2, the outlet OH may be located on the imaginary straight line VL.

The flow-dividing section 71 may be provided independently from the side wall of the humidifying tank 30. For example, the flow-dividing section 71 may be provided at the center of the inner space S when the humidifying tank 30 is seen in the first positive direction X1.

The size of the facing section 72 is not limited to the example in the embodiment described above. The facing section 72 may be omitted from the humidifying tank 30.

The facing section 72 may extend from a portion that is included in the outer peripheral surface 61F of the first passage 61 and that is nearer to the first end surface 61A than to the inlet IH. The facing section 72 need not extend parallel to the first axis X, and may extend toward the bottom wall 41 diagonally relative to the first axis X. It is sufficient that the facing section 72 has a part that overlaps the inlet IH when seen in the first negative direction X2. In this case, the aforementioned tumble flow can be generated at the part.

The facing section 72 need not have the facing surface 72A. For example, a portion that is included in the facing section 72 and that faces the flow-dividing section 71 may be a curved surface or a surface having protrusions and recesses.

The size of the shielding section 73 is not limited to the example in the embodiment described above.

In the embodiment described above, it is sufficient that a specific axis that intersects the bottom wall 41 is the vertical axis, and the vertical axis need not be orthogonal to the bottom wall 41.

Technological ideas that can be grasped from the embodiment and the modifications described above will be described.

<1> A CPAP apparatus comprising: a blower that pressurizes and feeds air; and a humidifying tank that allows air, pressurized and fed by the blower, to flow thereinto and has an inner space that is capable of storing water, wherein the humidifying tank includes a top wall, a side wall, and a bottom wall that define the inner space, a first passage through which the blower communicates with the inner space, a second passage through which the inner space communicates with a portion that is outside of the humidifying tank and that is different from the blower, a flow-dividing section that faces an inlet when the inlet is defined as an opening of the first passage on the inner space side, and a shielding section that extends toward the flow-dividing section from an end surface of the first passage on a side in which the inlet is open, wherein, when an outlet is defined as an opening of the second passage on the inner space side and a vertical axis is defined as a specific axis that intersects the bottom wall, as seen in a direction along the vertical axis, an opening center of the outlet is located so as to be displaced relative to an imaginary axis that passes through an opening center of the inlet and that is parallel to a direction in which the inlet faces, and wherein, when a specific end is defined as an end that is one of two ends of the inlet in a direction along an orthogonal axis orthogonal to the vertical axis and that is near the opening center of the outlet when the inlet is seen in a direction along the imaginary axis, the shielding section extends to the flow-dividing section from a portion that is included in the end surface and that is further toward an opposite side from the opening center of the inlet than the specific end.

<2> The CPAP apparatus described in <1>, wherein the first passage is curved when seen along the vertical axis, and wherein the specific end is located on an outer side of a curve of the first passage when seen along the vertical axis.

<3> The CPAP apparatus described in <2>, wherein the flow-dividing section is a part of the side wall.

<4> The CPAP apparatus described in any one of <1> to <3>, wherein a dimension of the shielding section in the direction along the vertical axis is ½ or more of a dimension of the inlet in the direction along the vertical axis.

<5> The CPAP apparatus described in any one of <1> to <4>, wherein the humidifying tank further includes a facing section that extends toward the bottom wall from an outer peripheral surface of the first passage, wherein the facing section includes a part that overlaps the inlet when seen along the vertical axis, and wherein the facing section faces the flow-dividing section.

<6> The CPAP apparatus described in <5>, wherein the facing section extends toward the bottom wall from a portion that is included in the outer peripheral surface of the first passage and that overlaps the inlet when seen along the vertical axis.

<7> The CPAP apparatus described in <5> or <6>, wherein the facing section includes a facing surface that is a surface facing in a direction that is the same as the direction in which the inlet faces.

<8> The CPAP apparatus described in <7>, wherein, when seen along the vertical axis, the outlet is located on an opposite side from the direction in which the inlet faces with respect to an imaginary straight line that extends on the facing surface.

What is claimed is:

1. A continuous positive airway pressure apparatus comprising:
    a blower configured to pressurize and feed air; and
    a humidifying tank configured to allow the air, pressurized and fed by the blower, to flow thereinto, the humidifying tank having an inner space capable of storing water,
    wherein the humidifying tank includes
        a top wall, a side wall, and a bottom wall defining the inner space,
        a first passage through which the blower communicates with the inner space,
        a second passage through which the inner space communicates with a portion being outside of the humidifying tank and being different from the blower,
        a flow-dividing section facing an inlet when the inlet is defined as an opening of the first passage facing the inner space, and a shielding section extending toward the flow-dividing section from an end surface of the first passage on a side in which the inlet is open, wherein, when an outlet is defined as an opening of the second passage facing the inner space and a vertical axis is defined as a specific axis intersecting the bottom wall, as seen in a direction along the vertical axis, an opening center of the outlet is located so as to be displaced relative to an imaginary axis passing through an opening center of the inlet and being parallel to a direction in which the inlet faces, and wherein, when a specific end is defined as an end being one of two ends of the inlet in a direction along an orthogonal axis orthogonal to the vertical axis and being nearer to the opening center of the outlet when the inlet is seen in a direction along the imaginary axis, the shielding section extends to the flow-dividing section from a portion included in the end surface and being further toward an opposite side from the opening center of the inlet than the specific end.

2. The continuous positive airway pressure apparatus according to claim 1, wherein the first passage is curved when seen along the vertical axis, and wherein the specific end is located on an outer side of a curve of the first passage when seen along the vertical axis.

3. The continuous positive airway pressure apparatus according to claim 1, wherein the flow-dividing section is a part of the side wall.

4. The continuous positive airway pressure apparatus according to claim 1, wherein a dimension of the shielding section in the direction along the vertical axis is ½ or more of a dimension of the inlet in the direction along the vertical axis.

5. The continuous positive airway pressure apparatus according to claim 1, wherein the humidifying tank further includes a facing section extending toward the bottom wall from an outer peripheral surface of the first passage, wherein the facing section includes a part overlapping the inlet when seen along the vertical axis, and wherein the facing section faces the flow-dividing section.

6. The continuous positive airway pressure apparatus according to claim 5, wherein the facing section extends toward the bottom wall from a portion included in the outer peripheral surface of the first passage and overlapping the inlet when seen along the vertical axis.

7. The continuous positive airway pressure apparatus according to claim 5, wherein the facing section includes a facing surface being a surface facing in a same direction as the direction in which the inlet faces.

8. The continuous positive airway pressure apparatus according to claim 7, wherein, when seen along the vertical axis, the outlet is located on an opposite side from the direction in which the inlet faces with respect to an imaginary straight line extending on the facing surface.

* * * * *